United States Patent [19]

Possis et al.

[11] Patent Number: 4,909,979
[45] Date of Patent: Mar. 20, 1990

[54] METHOD FOR MAKING A VASCULAR GRAFT

[75] Inventors: Zinon C. Possis; Demetre M. Nicoloff, both of Edina, Minn.

[73] Assignee: Possis Medical, Inc., Minneapolis, Minn.

[21] Appl. No.: 678,993

[22] Filed: Dec. 6, 1984

Related U.S. Application Data

[63] Continuation-in-part of Ser. No. 478,338, Mar. 24, 1983, Pat. No. 4,487,567.

[51] Int. Cl.$^4$ .............................................. B29C 57/00
[52] U.S. Cl. ..................................... 264/571; 264/573; 264/230; 264/232; 264/340; 264/342 R
[58] Field of Search ................... 264/342 R, 571, 554, 264/230, 573, 232, 340; 128/334 R

[56] References Cited

U.S. PATENT DOCUMENTS 4,126,659 11/1978 Blad ........................................ 249/65
4,546,499 10/1985 Possis et al. ......................... 128/1 R Primary Examiner—Hubert C. Lorin
Attorney, Agent, or Firm—Burd, Bartz & Gutenkauf

[57] ABSTRACT

A mandrel assembly supports an umbilical cord during the shaping and curing of the cord for use as a vascular graft. The mandrel assembly has a pair of mandrel members adapted to be releasably connected in end-to-end relation. Adjacent end sections of the mandrel members have reduced cross sectional shapes to provide the graft with a throat to restrict the flow of blood through the vascular graft. Each mandrel member has a low friction outer surface to facilitate the insertion and withdrawal of the mandrel member from the lumen of the umbilical cord. In one embodiment, the adjacent ends and neck portions of the mandrel members have small holes. A vacuum pump draws air from within the mandrel members to withdraw moisture from the tissue of the umbilical cord and hold the umbilical cord in conforming relationship with the joined mandrel members during the forming and curing of the umbilical cord.

21 Claims, 5 Drawing Sheets

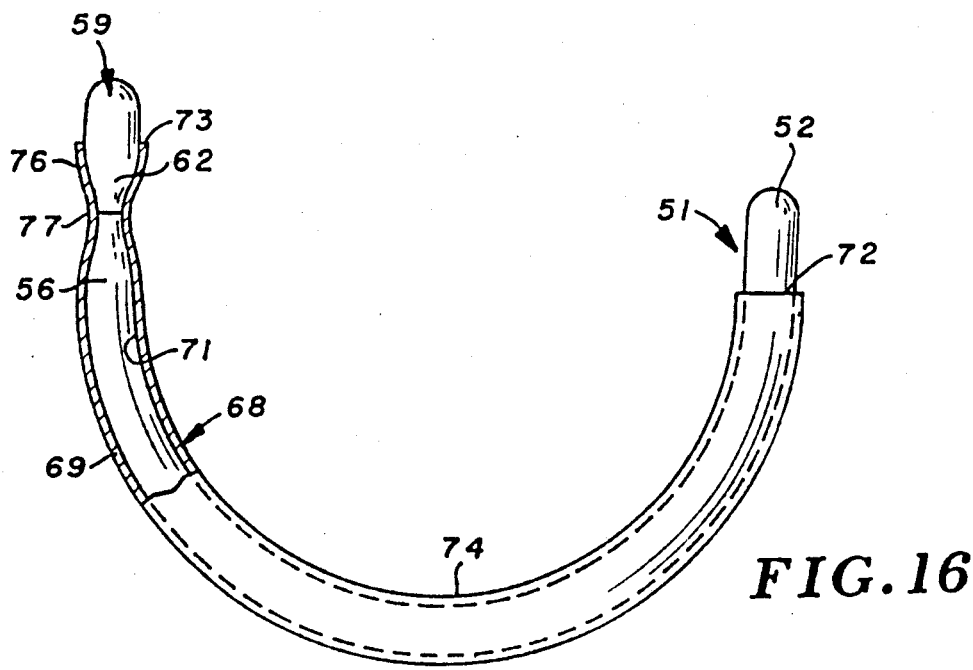
FIG.16
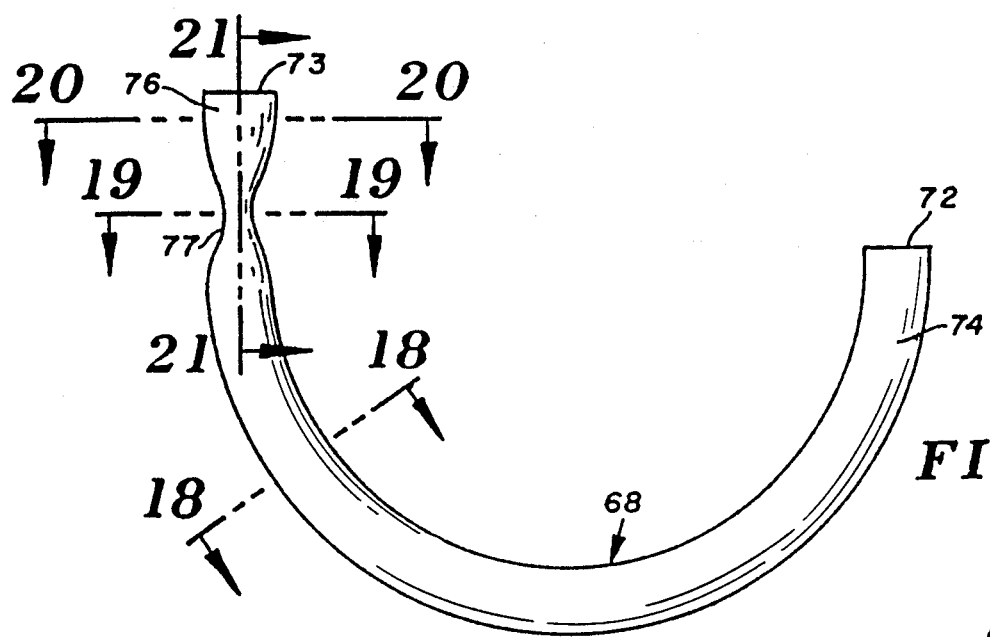
FIG.17
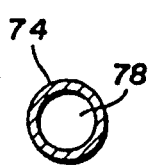  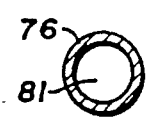 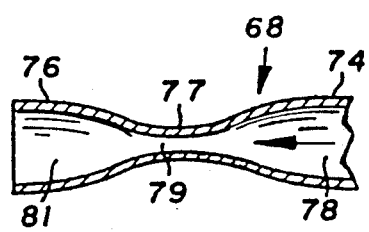
FIG.18  FIG.19  FIG.20  FIG.21

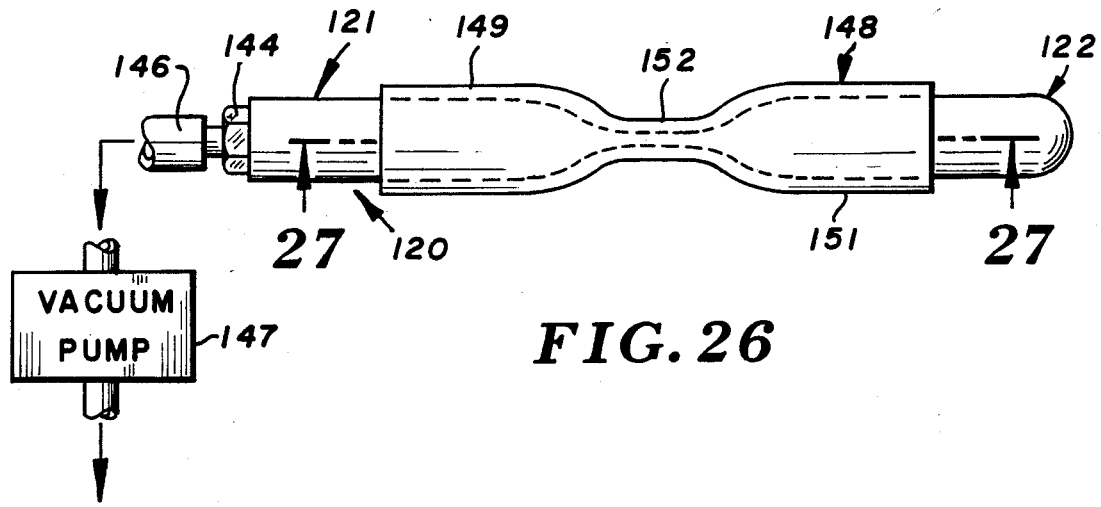
FIG. 26
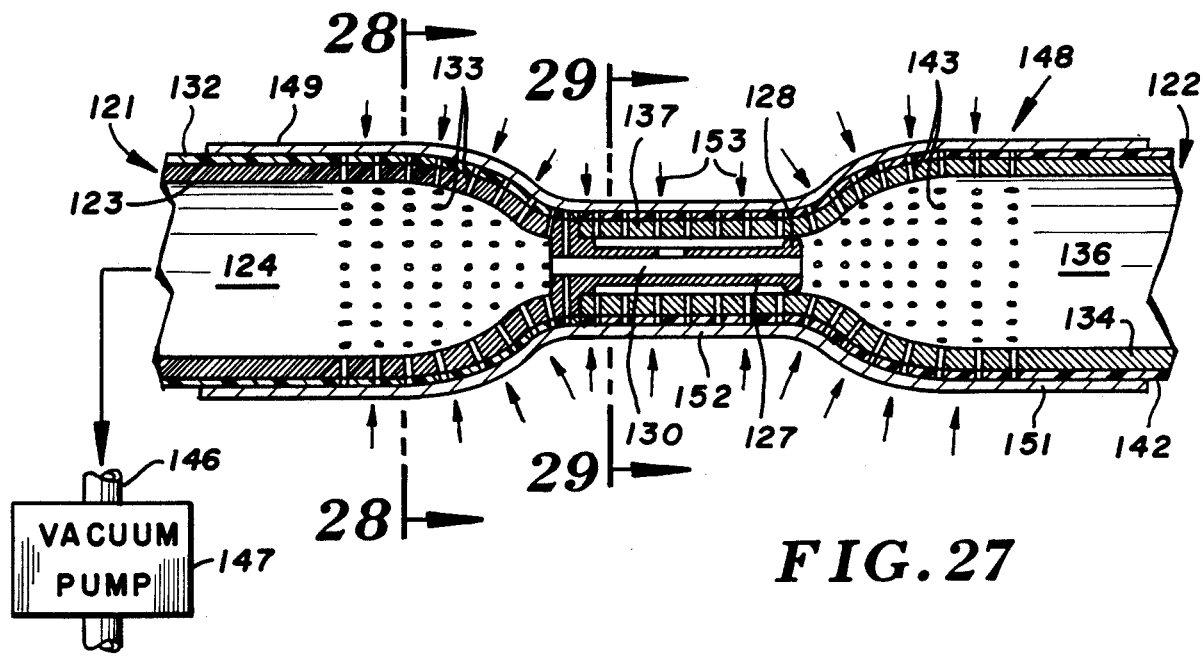
FIG. 27
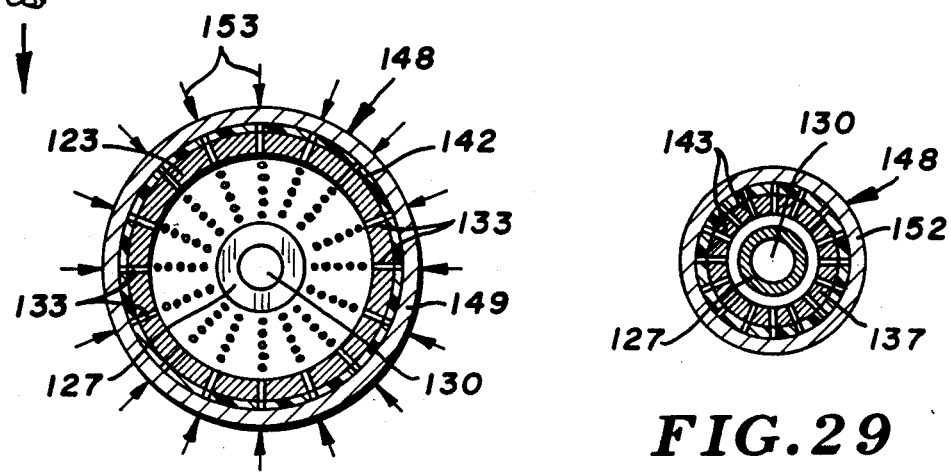
FIG. 28
FIG. 29

4,909,979

1

METHOD FOR MAKING A VASCULAR GRAFT

This is a continuation-in-part of Ser. No. 478,338, filed Mar. 24, 1983, Pat. No. 4,487,567.

FIELD OF INVENTION

The invention relates to a support for shaping a tubular member. More particularly, the support is a mandrel assembly for accommodating an umbilical cord for use as a vascular graft. The field of invention includes processes for forming and curing umbilical cords for use as vascular grafts.

BACKGROUND OF INVENTION

The use of human umbilical cords as vascular grafts in lieu of saphenous veins is disclosed in the prior art. The umbilical cords are processed for subsequent use in a living body. The umbilical cords are shaped and cured on a mandrel. Holman in U.S. Pat. No. 4,240,794 discloses a method of shaping a human umbilical cord to a configuration determined by a mandrel. The mandrel can have a J-shape or a U-shape. The umbilical cord is mounted on the mandrel and treated with alcohol to shrink the cord to the shape of the mandrel. An aldehyde solution is used to fix or cure the umbilical cords on the mandrel. The mandrel is then removed from the cured umbilical cord. The mandrel is a solid one-piece member of plastic, such as polyethylene. The plastic material of the mandrel is difficult to shape and machine to an accurate configuration. Accurate tolerances on plastic mandrels cannot be maintained. Metal mandrels are difficult to use to shape and cure umbilical cords, as these mandrels cannot be easily inserted into the lumen of an umbilical cord or withdrawn from a cured umbilical cord.

SUMMARY OF INVENTION

The invention broadly pertains to a mandrel assembly for supporting a tubular member to form and cure the tubular member to a vascular graft having a section for restricting the flow of fluid through the graft. The invention also includes a method of processing a human umbilical cord with a mandrel assembly for use as a vascular graft having a section for restricting the flow of fluid through the graft.

The mandrel assembly has a first mandrel member having a body and an end section located along a center line. The body and end section have an outer surface. The end section has a cross sectional area that is smaller than the cross sectional area of the body. A second mandrel member has a body and an end section located along the center line. The body and end section of the second mandrel member has an outer surface. The outer surfaces provides an elongated generally tubular shape used to determine the shape of the vascular graft. The end section of the second mandrel member has a cross sectional area smaller than the body attached thereto. This end section is shaped substantially the same as the cross sectional area and shape of the end section of the first mandrel member. Releasable means associated with the first and second mandrel members function to align the mandrel members, end sections, and outer surfaces, whereby the outer surfaces provide a support for an umbilical cord during the forming and curing thereof into a vascular graft having a section to restrict the flow of fluid through the graft. Each mandrel member has an outer flow friction coating means to facilitate the insertion and withdrawal of of the mandrel members from the umbilical cord. The coating means, such as polytetrafluoroethylene, provides the outer surfaces of the mandrel members with low friction characteristics. The coating means is secured to a metal core that defines the shape of the mandrel. The metal core has accurate tolerances and provides a rigid support for the coating means.

According to one embodiment of the mandrel assembly is used to form and cure a human umbilical cord into a vascular graft having a section for restricting the flow of fluid through the graft. First and second mandrel members have outer continuous layers of low friction means to facilitate the insertion and removal of the mandrel members from the umbilical cord. The mandrel members have adjacent end sections that are smaller in cross sectional area than the main body of the mandrel members. Each end section has a truncated cone portion and a generally cylindrical portion terminated in an end. The ends have cooperating means that releasably connect the first and second mandrel members together to align the outer surfaces thereof so that the outer surfaces provide support for an umbilical cord during the formation and curing of the cord into a vascular graft having a section to restrict the flow of fluid through the graft. The cooperating means comprise a tapered hole in one of the ends of the mandrel member and a tapered projection on the other end of the other mandrel member. The projection is of the size and shape to fit into the hole to releasably lock the first and second mandrel members together.

A second embodiment of the mandrel assembly is part of an apparatus used to form and cure a tubular member, such as an umbilical cord, into a vascular graft. Preferrably, the vascular graft has a throat section for maintaining a desired pressure of the fluid in the vascular graft while insuring a continuous flow of fluid through the vascular graft. The mandrel assembly has a first mandrel member having a first body and a first end section. The first body and first end section have a continuous outer surface. A plurality of small holes extend through the first end section into the mandrel member. A second hollow mandrel member has a second body and second end section. The second end section has a continuous outer surface that is co-extensive with the outer surface of the first end section. The second end section has a plurality of small holes. The first and second mandrel members have cooperating means for connecting the first and second end sections in end-to-end relation. The outer surfaces of the mandrel members provide shape and support for the tubular member during the forming and curing thereof into a vascular graft. A means for establishing a suction pressure, such as a vacuum pump, is connected in fluid communication with the first and second mandrel members to draw air and fluid through the first and second holes whereby the tubular member mounted on the mandrel members is subjected to a vacuum force. The vacuum force withdraws moisture from the tubular member and holds the tubular member in conforming relation with respect to the outer surfaces of the mandrel members during the forming and curing of the tubular member into a vascular graft. Each mandrel member is provided with an outer low friction coating to facilitate the insertion and withdrawal of the mandrel members from the tubular member and vascular graft.

The invention incudes the method of processing an umbilical cord for use as a vascular graft having a section for restricting the fluid flow through the graft. The method uses a mandrel assembly comprising first and second mandrel members having cooperating means to releasably connect the mandrel members together. The mandrel members also have means for making the section of the graft that restricts the flow of fluid through the graft. The method comprises the insertion of the first and second mandrel member into opposite ends of the uncured umbilical cord. The adjacent ends of the first and second mandrel members are connected together. The umbilical cord is then formed onto the outer surfaces of the mandrel members by shrinking the umbilical cord. This is accomplished with the use of alcohol, such as ethyl alcohol. The shrunk umbilical cord is then cured or fixed on the mandrel members with an aqueous solution of dialdehyde. The cured umbilical cord is then removed from the first and second mandrel members and stored in a preservative solution for subsequent use.

A further method of processing an umbilical cord for use in vascular graft is included in the invention. This method utilizes a mandrel assembly having first and second mandrel members adapted to be releasably connected to each other. The mandrel members have elongated hollow bodies when joined together forming a neck section having a cross sectional area smaller than the cross sectional area of the bodies of the mandrel members. The neck section as well as portions of the bodies of the mandrel members adjacent the neck section are provided with a plurality of small holes that are in communication with the interior passage of the mandrel members and the atmosphere. The process includes the insertion of the first mandrel member into one end of the lumen of an uncured umbilical cord. The second mandrel member is inserted into the other end of the lumen of the uncured umbilical cord. The adjacent ends of the first and second mandrel members are connected together to provide a neck section that is continuous with the bodies of the first and second mandrel members. A suction force established by a vacuum pump is applied to the first and second mandrel members to draw air from within the mandrel members and neck section. This holds the umbilical cord in surface conforming relation with the mandrel members and the neck section. The vacuum force also withdraws moisture and fluids from the umbilical cord. The vacuum force on the mandrel members is maintained during the forming of the umbilical cord by shrinking the cord onto the connected mandrel members. Alcohol can be used to shrink the umbilical cord. The umbilical cord is formed on the connected mandrel members and is secured or fixed. An aqueous solution of dialdehyde is used to cure the umbilical cord. After the umbilical cord is cured, the first and second mandrel members are removed from the opposite ends thereof. The cured cord is stored in a preservative solution for subsequent use as a vascular graft.

IN THE DRAWING

FIG. 16 is a side elevational view, partly sectioned, of the mandrel assembly of FIG. 12 supporting a human umbilical cord;

FIG. 17 is a side elevational view of the umbilical cord formed and cured on the mandrel assembly of FIG. 12 with the mandrel assembly removed from the cord;

FIG. 18 is an enlarged sectional view taken along the line 18—18 of FIG. 17;

FIG. 19 is an enlarged sectional view taken along the line 19—19 of FIG. 17;

FIG. 20 is an enlarged sectional view taken along the line 20—20 of FIG. 17;

FIG. 21 is an enlarged sectional view taken along the line 21—21 of FIG. 17;

FIG. 26 is a side view of the mandrel assembly of FIG. 22 coupled to a vacuum pump and accommodating an umbilical cord;

FIG. 27 is an enlarged sectional view taken along the line 27—27 of FIG. 26;

FIG. 28 is an enlarged sectional view taken along the line 28—28 of FIG. 27; and FIG. 29 is an enlarged sectional view taken along the line 29—29 of FIG. 27.

DESCRIPTION OF PREFERRED EMBODIMENTS

Referring to FIGS. 1–7, there is shown a first embodiment of the mandrel assembly of the invention indicated generally at 20. Mandrel assembly 20 is used to support a human umbilical cord during the forming and curing of the cord to provide a cord with a blood flow restrictor section. The forming and curing process of the umbilical cord is hereinafter described. Mandrel assembly 20 can be used to make the entire or a portion of the vascular graft, disclosed in U.S. Pat. No. 4,546,499. The disclosure of this U.S. Patent is included herein by reference.

Figure 7:
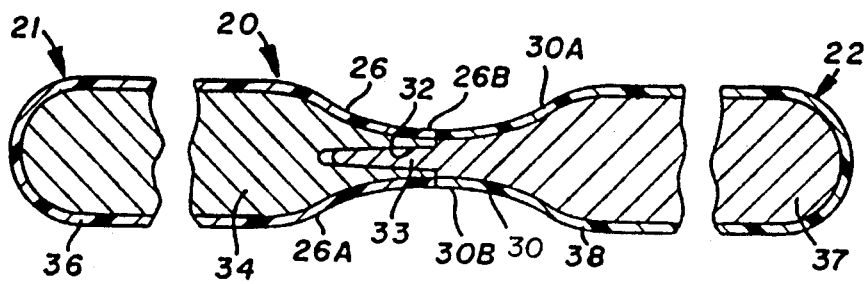
FIG. 7 is an enlarged foreshortened sectional view taken along the line 7—7 of FIG. 6.

Mandrel assembly 20 has a first elongated cylindrical member 21 releasably connected to a second elongated cylindrical member 22. First member 21 has an elongated linear cylindrical body 23 terminating in a semi-spherical outer end 24. The inner end of body 23 has a neck 26 terminating in a transverse annular inner end 27. As shown in FIG. 7, neck 26 has a truncated cone-shaped section 26A joined to a generally cylindrical section 26B. Section 26B has a diameter that is less than ½ the diameter of body 23. The diameter of the passage in section 26B can vary according to the throat size requirement of the vascular graft. For example, the diameter of the passage in section 26B can be 2 mm.

Figure 1:
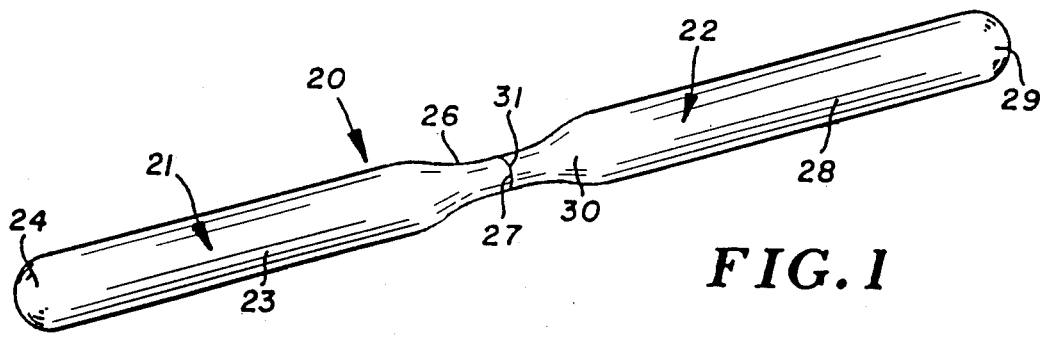
FIG. 1 is a perspective view of a mandrel assembly of the invention used to process and shape an umbilical cord for use as a vascular graft.
Figure 2:
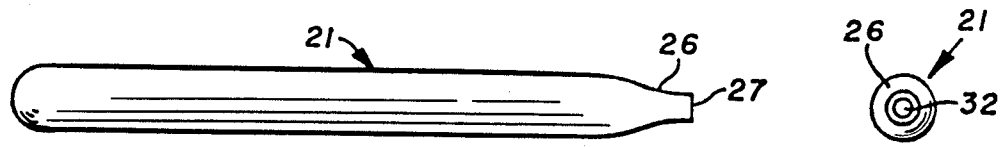
FIG. 2 is a side elevational view of a female mandrel section of the mandrel assembly of FIG. 1.
Figure 3:
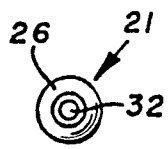
FIG. 3 is an end elevational view of the right end of FIG. 2.
Figure 5:
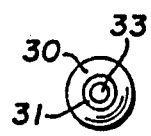
FIG. 5 is an end elevational view of the left end of FIG. 4.
Figure 4:
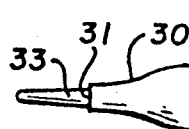
FIG. 4 is a side elevational view of a male mandrel section of the mandrel assembly of FIG. 1.
Figure 6:
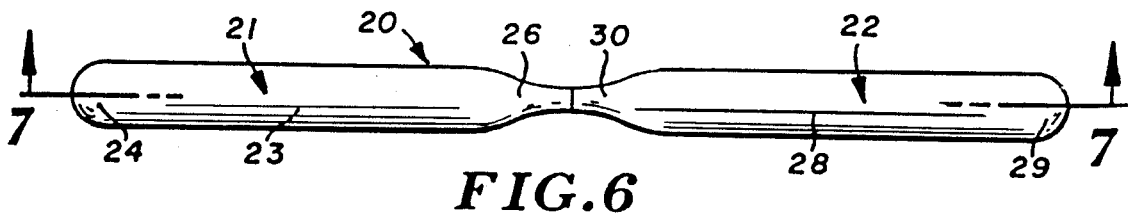
FIG. 6 is a side elevational view of the mandrel assembly.

The second member 22 has an elongated linear cylindrical body 28 having a semi-spherical shaped outer end 29. The inner end of body 28 has a neck 30 terminating in a transverse annular inner end 31. An axial finger or projection 33 extends along the longitudinal axis of member 22 away from end 31. Projection 33 has an outwardly converging taper of approximately 10 degrees relative to the longitudinal axis of body 28. The taper of projection 33 may be less than 10 degrees to facilitate inter-locking of the mandrel members 21 and 22 with each other. The outer end of projection 33 has a semi-spherical shape. As shown in FIG. 7, projection 33 fits into tapered hole 32 in neck 26 of mandrel member 21. Hole 32 is along the longitudinal axis of mandrel member 21 and tapers outwardly from the bottom end thereof. The taper of hole 32 is complementary to the taper of projection 33. Neck 30 has a truncated cone section 30A joined to a generally cylindrical section 30B. The section 30B has a diameter that is less than ½ the diameter of the body 28. The diameter of section 30B is substantially the same as the diameter of section 26B. When mandrel members 21 and 22 are assembled together, as shown in FIGS. 1, 6, and 7, ends 27 and 31 are in engagement with each other and cylindrical surfaces 26B and 30B are coextensive with each other.

Referring to FIG. 7, first member 21 has a cylindrical rigid inner portion or core 34 of metal, such as stainless steel. Core 34 is preferably solid metal, which can be machines to an accurate configuration. The outer surface of core 34 is covered with a coating or outer layer 36 of low friction plastic material, such as polytetrafluoroethylene, known by the Trademark TEFLON. Other low friction plastic material can be used to coat cores 34 and 37. The second member 22 has a solid metal core 37 covered with an outer coating or layer 38 of low friction plastic material, such as TEFLON. The plastic material is applied to cores 34 and 37 with a conventional process. The plastic outer layers 36 and 38 are thin, continuous, uniform in thickness and cover the entire outer surfaces of cores 34 and 37. The plastic material has a low coefficient of friction, which facilitates the insertion of the mandrel members 21 and 22 into the passage of a human umbilical cord. The plastic material is inert to umbilical cord tissue and the chemicals used to treat and cure the umbilical cord. The plastic outer layers 36 and 38 also facilitate the removal of the mandrel members 21 and 22 to form the formed and cured umbilical cord.

Figure 8:
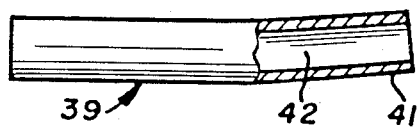
FIG. 8 is a side view, partly sectioned, of a human umbilical cord with the umbilical arteries and mesenchyme removed therefrom.

Referring to FIG. 8, there is shown a section of a human umbilical cord indicated generally at 39. The natural umbilical cord or funiculus umbilicalis has umbilical vessels embedded in loose mesenchyme or Wharton's jelly. The vessels comprise the umbilical vein and two umbilical arteries located around the vein. Cord 39 is a section of the umbilical vein comprising an elongated tubular wall 41 surrounding a continuous lumen or passage 42. The mesenchyme and umbilical arteries have been removed from the vein. Tubular wall 41 has a generally uniform diameter and must be formed and cured prior to its utilization as a vascular graft.

Figure 9:
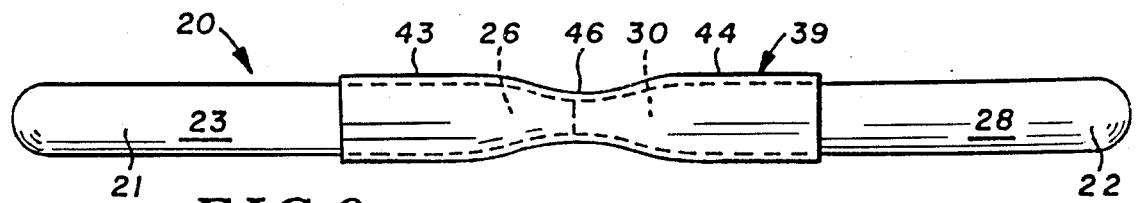
FIG. 9 is a longitudinal sectional view showing an umbilical cord mounted on the mandrel assembly.

Referring to FIG. 9, mandrel assembly 20 has been inserted into lumen 42 of umbilical cord 39. Mandrel members 21 and 22 are inserted into opposite ends of umbilical cord 39 until their adjacent ends 27 and 31 contact each other. Projection 33 fits into tapered hole 32 to lock members 21 and 22 together. The umbilical cord 39 has opposite end portions 43 and 44 that are expanded by the cylindrical bodies 23 and 28. The mid-section of the cord section 39 is shrunk down and fits over neck sections 26 and 30 of mandrel assembly 20. An umbilical cord having umbilical arteries and mesenchyme can be placed on the mandrel assembly 20. The umbilical arteries and mesenchyme are removed from the umbilical vein during the processing procedure. The umbilical cord 39 is then treated, cured, and formed. A method of preparing the human umbilical cords for use in vascular replacement is disclosed by Holman et al in U.S. Pat. No. 4,240,794. The human umbilical cord is initially flushed to remove loose tissue and other substances therefrom. The cord is mounted on mandrel assembly 20, as hereinafter described. The mandrel assembly 20 supporting the umbilical cord, as shown in FIG. 9, is immersed in ethyl alcohol for a period of time of at least 18 hours. The immersion in ethyl alcohol is maintained until the umbilical cord 39 is substantially dehydrated. The umbilical cord 39, during the dehydration, shrinks onto mandrel assembly 20. This forms the umbilical cord. A portion of the umbilical cord is shrunk down and fits over the neck sections 26 and 30 of mandrel assembly 20, thereby forming a Venturi throat section 46 in the umbilical cord 39. The dehydrated umbilical cord 39 mounted on mandrel assembly 20 is then immersed into an agueous solution of dialdehyde to cure or fix the umbilical cord 39. The umbilical cord 39 is treated with the aqueous solution for a period of time for about 18 hours. The cord 39 is then stored for subsequent use as a vascular graft. A mesh sleeve (not shown) can be placed over cord 39 to provide additional reinforcement for the wall of the cord. Mandrel assembly 20 can be used with other processes for removing the umbilical arteries, mesenchyme, and forming and fixing human umbilical cords for use as vascular grafts.

In use, umbilical cord 39 is located on mandrel assembly 20, as shown in FIG. 9. The neck end 26 of mandrel member 21 is inserted into one end of lumen 42. The neck end 30 of the second mandrel member 22 is inserted into the opposite end of lumen 42. The mandrel members 21 and 22 are longitudinally moved together into a locking relationship. The low friction plastic layers 36 and 38 of mandrel members 21 and 22 facilitate the slipping of the mandrel members 21 and 22 into the lumen of the umbilical cord. Projections 33 fits into tapered hole 32. The complementary tapers of hole 32 and projection 33 provide a self-locking action that holds mandrel sections 21 and 22 together. Umbilical cord 39 has expanded end portions 43 and 44 located about mandrel members 23 and 28. The center portion of umbilical cord 39 has a reduced cross sectional area throat section 46 located about engaging necks 26 and 30. The umbilical cord 39 on mandrel assembly 20, as shown in FIG. 9, is cured. During the curing process, tubular wall 41 of umbilical cord 39 is shaped in a manner determined by the shape of mandrel assembly 20.

Figure 10:
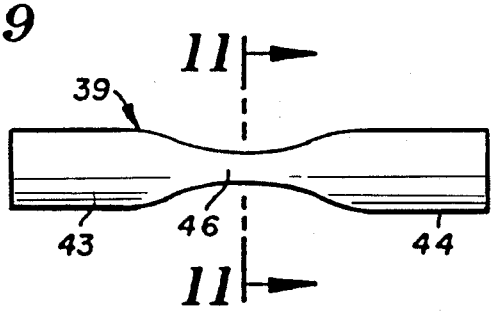
FIG. 10 is a side elevational view of the section of the umbilical cord having a reduced diameter throat to restrict blood flow through the cord made with the use of the mandrel assembly.
Figure 11:
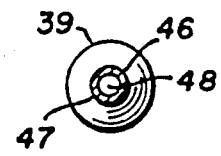
FIG. 11 is a sectional view taken along the line 11—11 of FIG. 10.
Figure 12:
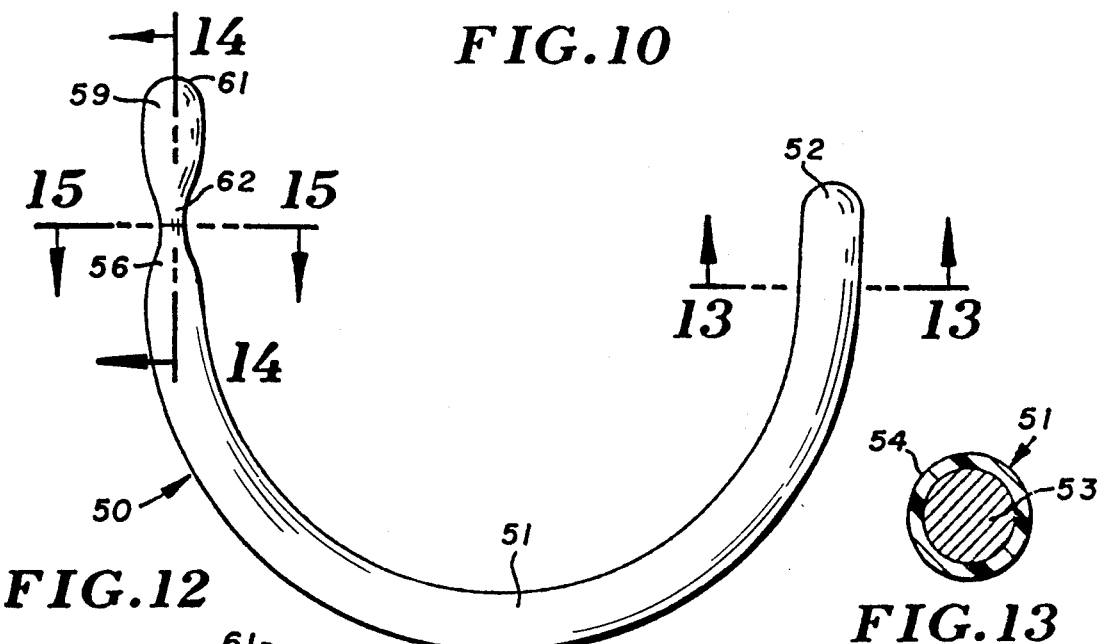
FIG. 12 is a side elevational view of a modified mandrel assembly of the invention used to process and shape an umbilical cord for use as a vascular graft.

The shape of the curved umbilical cord 39 is shown in FIG. 10. The throat section 46 of umbilical cord 39 has a generally cylindrical wall 47 surrounding a passage 48. The passage 48 is in longitudinal communication with the passages in the opposite ends of the umbilical cord 39 so as to allow continuous blood flow through the cured umbilical cord 39. Passage 48 is a throat having a cross sectional area that is substantially less than the cross sectional area of the passages in the end sections 43 and 44. Preferably, the cross sectional area of passage 48 is less than ¼ of the cross sectional area of the lumen of sections 43 and 44. The cross sectional areas of sections 43 and 44 are substantially the same. For example, the cross sectional area of the body passage can be 19.6 mm$^2$ and the cross sectional area of the passage of throat section 48 can be 3.14 mm$^2$. Other cross sectional area sizes of the lumen can be made on mandrel assembly 20.

Figure 13:
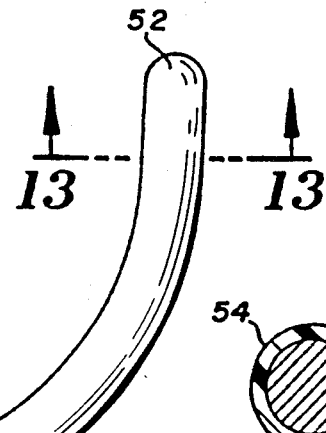
FIG. 13 is an enlarged sectional view taken along the line 13—13 of FIG. 12.
Figure 14:
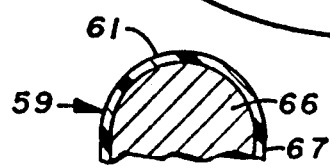
FIG. 14 is an enlarged foreshortened sectional view taken along the line 14—14 of FIG. 12.
Figure 14:
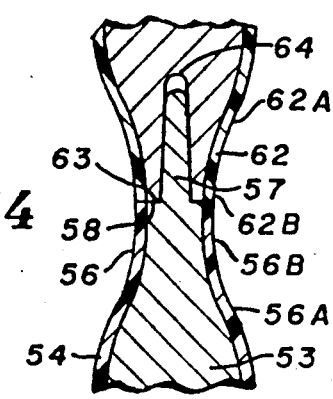
Figure 15:
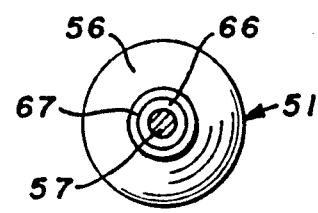
FIG. 15 is an enalrged sectional view taken along the line 15—15 of FIG. 12.
Figure 22:
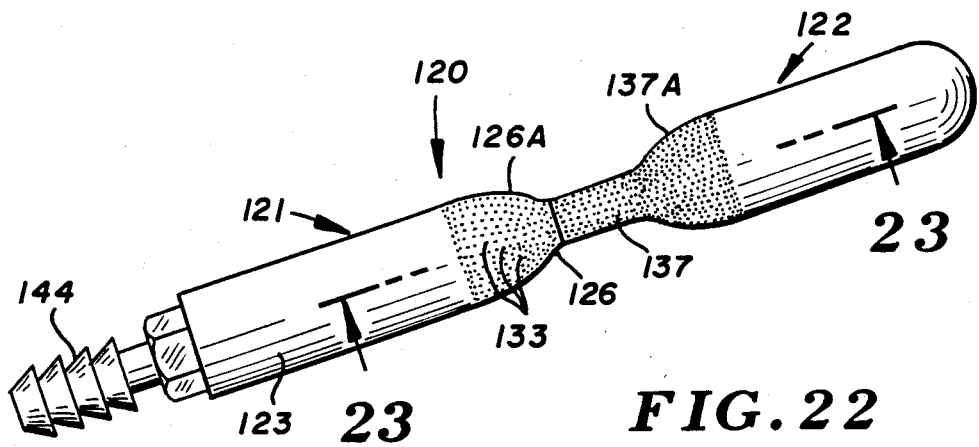
FIG. 22 is a perspective view of another modification of the mandrel assembly of the invention used to process an umbilical cord for use as a vascular graft.

Referring to FIGS. 12-15, there is shown a second embodiment of the mandrel assembly of the invention indicated generally at 50 for accommodating a human umbilical cord during forming and curing thereof. Mandrel assembly 50 has a first generally U-shaped mandrel member 51 releasably connected to a second mandrel member 59. Mandrel member 51 has a semi-spherical proximal end 52 and a neck or distal end 56. Mandrel member 51 has a U-shaped curved metal core 53. The entire outer surface of core 53 is shown in FIGS. 13 and 14 as coated with a layer of low friction plastic material 54, such as polytetrafluoroethylene, known as TEFLON, to facilitate the insertion and removal of the mandrel members 51 and 59 into and from the umbilical cord 68. As shown in FIG. 14, neck end 56 has a projection 57 extended outwardly along the longitudinal axis or center line of neck end 56. Projection 57 is generally cone-shaped and has an outwardly directed converging taper. The diameter of the base of projection 57 is smaller than the diameter of the end of the neck end 56. An annular generally flat end wall 58 surrounds the base of projection 57. Coating layer 56 extends to end wall 58. Neck end 56 has a generally truncated cone section 56A that is joined to a cylindrical section 56B.

The second mandrel member 59 has a semi-spherical outer end 61 and a neck end 62 opposite the end 61. Neck end 62 has a truncated cone section 62A joined to a cylindrical section 62B. The section 62B terminates in a flat end 63 having a tapered longitudinal hole 64. Hole 64 and projection 57 have a complementary converging taper. Preferably, the taper is 10 degrees or less so that the projection locks into hole 64 when second mandrel member 59 is placed in assembled relation with the first mandrel member 51. Mandrel member 59 has a metal core 66. The outer surface of core 66 is covered with a coating layer 67, such as a low friction plastic material, as polytetrafluoroethylene.

Referring to FIG. 16, there is shown mandrel assembly 50 in assembled relation with an umbilical cord 68 to provide a support for the process to form and cure the umbilical cord 68. First mandrel member 51 is inserted through end 72 of umbilical cord 68. The inside diameter of the umbilical cord is slightly expanded. The neck end 56 is located inwardly of the umbilical cord end 73. The second mandrel member 59 is inserted into end 73. After the umbilical cord 68 is cured, the mandrel members 51 and 59 are withdrawn from the opposite ends of the cured umbilical cord. The low friction coating layers 54 and 67 have continuous outer surfaces that facilitate the insertion of the mandrel members 51 and 59 into the opposite ends of the umbilical cord and the extraction of the mandrel members 51 and 59 from the cured and formed umbilical cord.

As shown in FIGS. 17-21, the cured umbilical cord 68 has a body or proximal section 74 extended from the proximal end 72 to throat section 77. Throat section 77 is joined to distal section 76. Distal section 76 terminates at distal end 73. Proximal section 71 has a passage 78 leading to a throat passage 79 surrounded by throat section 77. Passage 79 is open to a distal passage 81. The cross sectional area of throat section 79 is substantially smaller than the cross sectional area of the proximal passage 78. The cross sectional area of proximal passage 81 is substantially the same as the cross sectional area of the proximal passage 78. The umbilical cord having the throat section 77 is used as a vascular graft in the manner disclosed in U.S. Pat. Nos. 4,546,499 and 4,601,718. The disclosures of these Applications are incorporated herein by reference.

Referring to FIGS. 22 to 25, there is shown a third embodiment of the mandrel assembly of the invention indicated generally at 120. Mandrel assembly 120 is used to support a human umbilical cord during the forming and curing of the cord for use as a vascular graft. The umbilical cord is provided with a blood flow restrictor section in the distal end section thereof as hereinafter described. Mandrel assembly 120 can be used to make the entire or a portion of the vascular graft as disclosed in U.S. Pat. Nos. 4,546,499 and 4,601,718. The disclosures of these applications are included herein by reference.

Mandrel assembly 120 has a first elongated mandrel member 121 releasably connected to a second elongated mandrel member 122. First member 121 has a linear tubular member body 123 having an internal passage 124. The inner end of body 123 has a neck 126 having a cross sectional size that is smaller than the cross sectional size of body 123. A truncated cone-shaped section 126A joins body 123 to neck 126. An elongated tubular projection 127 extends linearly from neck 126. The outer end of projection 127 has an outwardly directed annular bead or ring 128. The inner end of projection 127 has an outwardly directed annular shoulder 129. A passage 130 extends through tubular projection 127. The mid-portion of projection 127 has a hole 131 open to an annular chamber 138. The outside surface of body 123 and neck 126 is covered with an outer layer or coating of 132 of low friction plastic material, such as polytetrafluoroethylene, known by the trademark TEFLON. Other low friction plastic materials can be used to coat the outside of first and second mandrel members 121 and 122. The low friction plastic material facilitates the insertion of mandrel members 121 and 122 into the lumen of a human umbilical cord. The plastic material is inert to the tissue of the umbilical cord and the chemicals used to treat and cure the umbilical cord. The low friction layer 132 also facilitates the removal of each mandrel member 121 and 122 from the formed and cured umbilical cord.

The inner end of body 123 has a plurality of holes 133 that extend from passage 124 through outer layer 132. A plurality of holes are located in neck 126 and cone section 126A at the inner end of mandrel member 121. Holes 133, as shown in FIG. 28, are evenly spaced around the inner end of mandrel member 121. The holes 133 are relatively small and preferably have a diameter smaller than 0.15 mm. A laser drilling process can be used to make holes 133 and 143. Porous material can be used in lieu of the drilled inner ends of the mandrel members.

Figure 23:
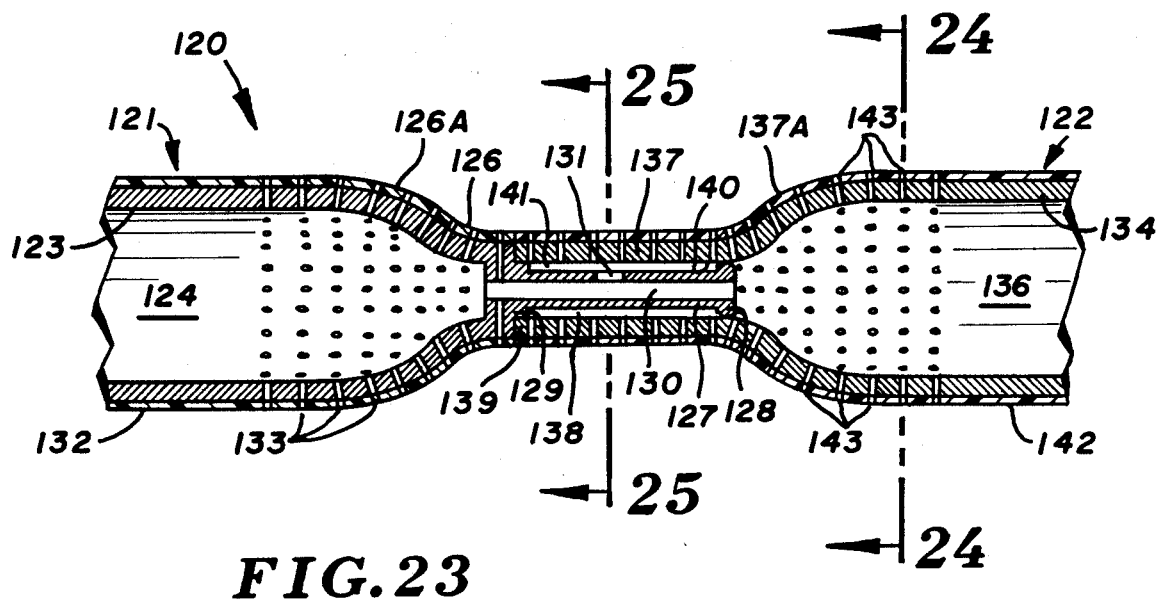
FIG. 23 is an enlarged sectional view taken along the line 23—23 of FIG. 22.
Figure 24:
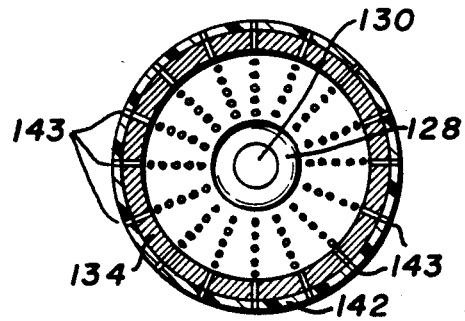
FIG. 24 is an enlarged sectional view taken along the line 24—24 of FIG. 23.
Figure 25:
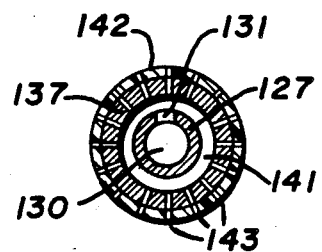
FIG. 25 is an enlarged sectional view taken along the line 25—25 of FIG. 23.

Second mandrel member 122 has an elongated tubular body 134 provided with an internal chamber 136. The inner end of the body 134 tapers down and forms an elongated neck 137. The neck 137 has a cylindrical section and a truncated cone 137A that is complementary to cone section 126A. As shown in FIG. 23, neck 127 has a linear passage 138 and a flat annular end 139. Projection 127 forms with inner wall 140 of neck 137 a annular chamber 141. When mandrel members 121 and 122 are joined together, projection 127 fits in passage 138. The annular bead 128 is in light frictional engagement with the inner wall 140. The end 138 fits on the annular shoulder 129. Bead 128 and shoulder 129 can have tapering surfaces to facilitate the locking of the mandrel members 121 and 122 together. Body 134 and neck 137 are covered with an outer layer of low friction material 142. The low friction material is the same type of material as layer 132. The inner end of body 134 and the neck 137 are provided with a plurality of small holes 143. As shown in FIGS. 23 to 25, the holes 143 extend through the outer layer 142 and are open to the chambers 136 and 141.

Preferably, the cross sectional area of neck 137 is less than one quarter of the cross sectional area of body 134. The cross sectional area of body 134 can be the same as or less than the cross sectional area of the body 123. Preferably, the cross sectional areas of bodies 123 and 134 are substantially the same. For example, the cross sectional area of body 134 can be 19.6 mm$^2$ and the cross sectional area of the neck can be 3.14 mm$^2$. Other cross sectional area of the bodies and necks can be used to provide the umbilical cord with a reduced sized throat section for controlling the flow and pressure of the fluid through the vascular graft.

A vacuum pump 147 is connected with a suitable hose 146 to a fitting 144 on the outer end of mandrel member 121. The vacuum pump 147 is operable to evacuate the passage 142 and chambers 136 and 141 within mandrel members 121 and 122. Air is drawn through the holes 133 and 143.

Uncured umbilical cords are stored in a preservative liquid solution located in tubular containers. An umbilical cord is removed from the stored solution and flushed with a saline solution to remove any loose tissue and other substances therefrom. The entire umbilical cord 148 is mounted on mandrel assembly 120. As shown in FIGS 26 to 29, the uncured umbilical cord indicated generally at 148 is placed on each of mandrel members 121 and 122. Umbilical cord 148 has a first section 149, a second section 151 and a reduced cross section neck section 152 joining the first and second sections 149 and 151. Mandrel members 121 and 122 are inserted or slipped into opposite ends of the lumen of umbilical cord 148. The projection 127 is moved into passage 138 until the necks of the mandrel members 121 and 122 are in full engagement with each other as shown in FIG. 27. The low friction coating material 132 and 142 facilitates the movement of mandrel members 121 and 122 into the opposite ends of the lumen of umbilical cord 148. The first and second sections 149 and 151 of the umbilical cord 148 are slightly expanded and fit on the large cylindrical inner end sections of the mandrel bodies 123 and 134. The neck section 152 of umbilical cord 148 is located about the reduced cross section neck 137. The uncured umbilical cord takes the shape of the mandrel assembly 120.

The mesenchyme and umbilical arteries on the umbilical cord are removed from the outside of the umbilical cord. This is done after the umbilical cord is mounted on the mandrel members 121 and 122. The mesenchyme and umbilical arteries can be removed by abrasion, liquid jet cutting and laser vaporization procedures.

The application of vacuum or suction force to the interior of mandrel assembly 120 by the vacuum pump 147 draws umbilical cord 148 into tight conforming surface engagement with the outer low friction layers 132 and 142 of mandrel assembly 120, as shown by arrows 153 in FIG. 27. The neck section 152 and convex curved cone shaped portions at the opposite ends of the neck section 152 of the umbilical cord are continuously subjected to the suction force which draws these sections of the umbilical cord circumferentially inward into conforming relation with the outer surface of the mandrel assembly. The umbilical cord 148 is continuously retained in firm surface engagement with the low friction layers 132 and 142 of mandrel assembly 120 by the suction force within the mandrel members 121 and 122. Vacuum pump 147 is operable to withdraw the air from passage 124 in chamber 136. A vacuum of between 22 to 27 inches of Hg is applied. The numerous holes 133 and 143 provide a network of openings which firmly hold the tissue of umbilical cord 148 on the inner end sections and neck section mandrel members 121 and 122. The continuous suction force on the umbilical cord draws moisture and liquids from the tissue of the umbilical cord.

The mandrel assembly 120, along with umbilical cord 148 thereon is immersed in a ethanol solution for dehydration. This removes the water and other liquids from the tissue of the umbilical cord and shrinks the umbilical cord on the mandrel assembly 120. The solution is preferably 95% ethanol solution. Other alcohols, such as ethyl alcohol, can be used to dehydrate the umbilical cord. The suction force is continuously applied to the mandrel assembly 120 during the dehydration procedure. The ethanol solution is drawn into and through the tissue of the umbilical cord. This facilitates the dehydration process and shrinking of the umbilical cord on the mandrel assembly. The immersion of the umbilical cord in the ethanol solution is for a period of time required to achieve substantial dehydration. This period of time may be up to 18 hours.

The umbilical cord 148 along with mandrel assembly 120 is then immersed in a tissue fixation solution, such as an aqueous solution of dialdehyde starch. The treatment in the fixation solution can be for a period of time for about 18 hours. During the dehydration and fixation processes, the vacuum or suction force on the mandrel assembly 120 and umbilical cord is continuously maintained. The umbilical cord 148 is cured airtight to the outside shape of the mandrel assembly 120. During the dehydration and fixing of the umbilical cord on the mandrel assembly 120 the tissue of the cord section 152 is circumferentially compressed and compact around neck 137. Cord section 153 is strong and relatively nonelastic so as to maintain its reduced cross sectional area during use.

Following the fixation of umbilical cord 148 on mandrel assembly 120, the vacuum pump 147 is turned off. Mandrel members 121 and 122 are separated from each other and removed from the opposite ends of the cured umbilical cord. The formed umbilical cord 148 is placed in an alcohol and propylene oxide solution and stored for subsequent use as a vascular graft.

While there has been shown and described three embodiments of the mandrel assembly and methods of forming and curing a human umbilical cord for use as a vascular graft of the invention, it is understood that changes in the size, shape, length of the mandrel members and changes in the process steps may be made by those skilled in the art without departing from the invention. The invention is defined in the following claims.

The embodiments of the invention in which an exclusive property or privilege is claimed are defined as follows:

1. A method of processing an umbilical cord having open opposite ends for use as a vascular graft having a section for restricting fluid flow through the graft with a mandrel assembly comprising first and second mandrel members having cooperating means to releasably connect the mandrel members together, and means for making the section for restricting fluid flow through said graft comprising: inserting the first mandrel member into one end of the lumen of an uncured umbilical cord, inserting the second mandrel member into the other end of the lumen of the uncured umbilical cord, connecting the first and second mandrel members together with said cooperating means, forming said umbilical cord by shrinking said umbilical cord onto said connected first and second mandrel members and means for making the section for restricting fluid flow through said graft whereby the umbilical cord conforms to the shape of the connected mandrel members, curing the formed umbilical cord on the first and second mandrel members and said means for making the section for restricting fluid flow through said graft, and removing the first and second mandrel members from said one end and other end of the cured umbilical cord.

2. The method of claim 1 wherein: said umbilical cord is formed by subjecting the uncured umbilical cord to alcohol to shrink the umbilical cord on the connected first and second mandrel members.

3. The method of claim 1 wherein: the formed umbilical cord is cured with an aqueous solution of dialdehyde.

4. The method of claim 1 including: removing the mesenchyme and umbilical arteries from the outside of the uncured umbilical cord that is located on the connected mandrel members before the forming thereof.

5. The method of claim 1 including: flushing the uncured umbilical cord with a saline solution to remove loose tissue therefrom before insertion of the mandrel members into the lumen thereof.

6. The method of claim 1 including: applying a suction force to the interior of the connected first and second mandrel members to draw the umbilical cord into conforming relation with the connected mandrel members.

7. The method of claim 6 wherein: the suction force is continuously maintained on the umbilical cord during the forming and curing of the umbilical cord.

8. A method of processing an umbilical cord having open opposite ends for use as a vascular graft, said vascular graft having a section having a reduced cross sectional area for controlling the flow of liquid through the graft and the pressure of the liquid in the graft, with a mandrel assembly having first and second mandrel members adapted to be releasably connected to each other, said mandrel members having elongated hollow bodies when joined together forming a neck section having a cross sectional area smaller than the cross sectional area of a body, said bodies and neck section having a plurality of holes extended therethrough, comprising: inserting the first mandrel member into one end of the lumen of an uncured umbilical cord, inserting the second mandrel member into the other end of the lumen of the uncured umbilical cord, joining the first and second mandrel members together to provide the neck section, applying a suction force to the interior of the first and second mandrel members to draw air from within the mandrel members and neck section and hold the umbilical cord in surface conforming relation with the mandrel members and neck section thereof, forming said umbilical cord by shrinking said cord onto the joined mandrel members and neck section thereof, curing the formed umbilical cord on the joined mandrel members and neck section thereof, and removing the first and second mandrel members from the one end and other end of the cured umbilical cord.

9. The method of claim 8 including: removing the mesenchyme and umbilical arteries from the outside of the uncured umbilical cord that is located on the connected mandrel members before the forming thereof.

10. The method of claim 8 wherein: said umbilical cord is formed by subjecting the uncured umbilical cord to alcohol to shrink the umbilical cord on the connected first and second mandrel members.

11. The method of claim 10 wherein: the suction force is applied to the connected mandrel members and neck section during the forming of the umbilical cord.

12. The method of claim 8 wherein: the formed umbilical cord is cured with an aqueous solution of dialdehyde.

13. The method of claim 12 wherein: the suction force is applied to the connected mandrel members and neck section during the curing of the umbilical cord.

14. The method of claim 8 wherein: the suction force is continuously applied to the connected mandrel members and neck section during the forming and curing of the umbilical cord.

15. A method of processing an umbilical cord having open opposite ends for use as a vascular graft with a mandrel assembly having first and second mandrel members adapted to be releasably connected to each other, comprising: inserting the first mandrel member into one end of the lumen of an uncured umbilical cord, inserting the second mandrel into the other end of the lumen of the uncured umbilical cord, connecting adjacent portions of the first and second mandrel members together with the umbilical cord located thereon, forming said umbilical cord by shrinking said umbilical cord onto said connected first and second mandrel members, curing the formed umbilical cord on the first and second mandrel members, and removing the first and second mandrel members from one end and the other end of the cured umbilical cord.

16. The method of claim 15 wherein: said umbilical cord is formed by subjecting the uncured umbilical cord to alcohol to shrink the umbilical cord on the connected first and second mandrel members.

17. The method of claim 15 wherein: the formed umbilical cord is cured with an aqueous solution of dialdehyde.

18. The method of claim 15 including: removing the mesenchyme and umbilical arteries from the outside of the uncured umbilical cord that is located on the connected mandrel members before the forming thereof.

19. The method of claim 15 including: flushing the uncured umbilical cord with a saline solution to remove loose tissue therefrom before insertion of the first and second mandrel members into the lumen thereof.

20. The method of claim 15 including: applying a suction force to the interior of the connected first and second mandrel members to draw the umbilical cord into conforming relation with the connected mandrel members.

21. The method of claim 20 wherein: the suction force is continuously maintained on the umbilical cord during the forming and curing of the umbilical cord.

* * * * *